United States Patent
Kusaka et al.

(10) Patent No.: US 7,434,449 B2
(45) Date of Patent: Oct. 14, 2008

(54) EXHAUST GAS ANALYZER

(75) Inventors: Takeshi Kusaka, Kyoto (JP); Akihiro Taniguchi, Kyoto (JP); Kaoru Okada, Kyoto (JP); Tatsuki Kumagai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/288,531

(22) Filed: Nov. 29, 2005

(65) Prior Publication Data

US 2006/0144124 A1 Jul. 6, 2006

(30) Foreign Application Priority Data

Nov. 30, 2004 (JP) ............................. 2004-346236
Nov. 30, 2004 (JP) ............................. 2004-347018

(51) Int. Cl.
G01N 7/00 (2006.01)
G01N 1/24 (2006.01)
(52) U.S. Cl. .................. 73/23.31; 73/23.32; 73/23.33; 73/863.03; 73/863.51
(58) Field of Classification Search ............. 73/23.31, 73/23.32, 23.33, 863.02, 863.03, 863.81, 73/863.51
See application file for complete search history.

(56) References Cited

U.S. PATENT DOCUMENTS

| 4,633,706 | A | | 1/1987 | Ito et al. |
| 4,747,297 | A | | 5/1988 | Okayama et al. |
| 4,916,384 | A | | 4/1990 | Ishida et al. |
| 5,469,731 | A | * | 11/1995 | Decker et al. ............. 73/23.31 |
| 5,531,105 | A | * | 7/1996 | Leong et al. ................. 73/116 |
| 5,546,788 | A | * | 8/1996 | Dickow .................... 73/28.01 |
| 5,569,838 | A | * | 10/1996 | Broedel et al. ............ 73/23.31 |
| 5,709,082 | A | * | 1/1998 | Harris et al. ................. 60/276 |
| 5,739,413 | A | | 4/1998 | Kohn et al. |
| 6,405,577 | B2 | * | 6/2002 | Hanashiro et al. ......... 73/23.31 |
| 6,435,019 | B1 | * | 8/2002 | Vojtisek-Lom ............ 73/118.1 |
| 6,959,590 | B2 | * | 11/2005 | Hendren et al. ........... 73/118.1 |
| 2001/0029775 | A1 | * | 10/2001 | Uchihara et al. .......... 73/28.01 |
| 2004/0074319 | A1 | * | 4/2004 | Silvis et al. ............. 73/864.73 |

FOREIGN PATENT DOCUMENTS

| JP | 7-18243 | 3/1995 |
| JP | 09-005299 | 1/1997 |
| JP | 09318504 | 12/1997 |
| JP | 10090228 | 10/1998 |
| JP | 11-014530 | 1/1999 |

OTHER PUBLICATIONS

Partial European Search Report; Application No. EP 05 02 6139; May 16, 2006; European Patent Office.

* cited by examiner

*Primary Examiner*—Michael Cygan
(74) *Attorney, Agent, or Firm*—Brooks Kushman P.C.

(57) ABSTRACT

An SOF measuring system that can continuously measure SOF and a soot measuring system that can continuously measure soot are connected with an exhaust gas line. The soot measuring system comprises a diluter that selectively dilutes either one of the exhaust gas and standard gas whose hydrocarbon concentration is known with diluent gas and extrudes it. A dilution ratio adjusting device can adjust a dilution ratio of the diluter. A soot detector continuously detects soot in the exhaust gas or the standard gas diluted by the diluter. The SOF measuring system can be connected with the diluter so that an exhaust gas analyzer can measure the hydrocarbon concentration in the standard gas diluted by the diluter.

13 Claims, 7 Drawing Sheets

EXHAUST GAS ANALYZER

BACKGROUND OF THE INVENTION

1. Field of the Invention

This invention relates to an exhaust gas analyzer used for continuously measuring particulate matters (PM) included in exhaust gas of a diesel engine of, for example, a vehicle.

2. Background Art

Minute particulate matters (PM) that might cause an adverse effect on the environment or human health are contained in exhaust gas of an internal combustion engine such as a diesel engine, and soot and soluble organic fraction (SOF) or the like are mixed in the particulate matters.

In order to improve the internal combustion engine so as to reduce the particulate matters, it is necessary to measure the PM emissions accurately. According to a method for measuring exhaust gas that is publicly specified by the requirement of current laws and regulations, it is specified that the PM is collected by a filter and the collected PM is weighted on a microbalance.

However, since it is impossible for this method to collect the generating PM dynamically, there is a demand for a simple measurement instrument that is capable of a real-time continuous PM measurement in a step of research and development of an internal combustion engine. Furthermore, recently since the PM emission is considerably decreasing due to improvement of the internal combustion engine, a demand for measuring a minute amount of PM emissions has been increasing in addition to the continuous measurement.

Regarding SOF, a method has been developed that can continuously and accurately measure concentration of liquefied or solidified particulate hydrocarbon (SOF) in exhaust gas at a certain reference temperature (47° C.±5° C.) by the use of a detector high-sensitive to hydrocarbon such as a flame ionization detector (FID).

Regarding soot, the inventors have been developing a high-sensitive soot detector that can perform continuous measurement by making use of a diffusion charge detecting method.

This kind of a soot detector requires that the exhaust gas be diluted to concentration appropriate to the exhaust gas measurement because it is high sensitive, however, there are the following problems in diluting the exhaust gas.

First, it is required to grasp a dilution ratio in order to calculate the concentration of soot in the original exhaust gas based on the concentration of soot in the measured diluted exhaust gas.

However, in order to obtain the dilution ratio if the soot detector has an arrangement wherein a flow of the exhaust gas prior to dilution and a flow of the exhaust gas after dilution are measured respectively by the use of a venturi meter and the dilution ratio is calculated based on the flow ratios, the soot detector becomes large and costly.

Secondly, it is preferable that the dilution ratio by the diluter can be changed with ease because the concentration of soot in the exhaust gas is affected to change by a variety or a state of the internal combustion engine.

However, if the exhaust gas as being sample gas or the diluent gas is forcefully fed or sucked by the use of, for example, a rotary pump in order for dilution, a bad influence might be exerted upon soot measurement such that an unexpected portion is clogged with soot because the fluid path inside the pump is complicated. In addition, the rotary pump is not suitable for accurate soot measurement because of pulsation generating in the diluted exhaust gas.

On the contrary, an ejector that conducts liquid transfer by making use of an involute action of fluid blowing out due to bounded jet has a simple flow path and there is no pulsation generating. Then the ejector can be used as a diluter that is very preferable for this kind of measurement.

However, generally it is considered that the ejector can not change a dilution ratio arbitrarily (if a lot of diluent gas is flowed, pressure in a nozzle diffuser part decreases and the flow volume of the sample gas increases by just this much and consequently the dilution ratio does not change significantly), the ejector has a problem with this point. Conversely, the ejector is often used in a case that the dilution ratio is to be kept to some extent or in a case that the dilution ratio is not cared at all (for example, a pump).

As mentioned, the ejector has a merit that the flow path is simple and free from pulsation, however, it is considered that it has a demerit that the dilution ratio can not be adjusted easily when used as a diluter. As a result, it is difficult to use the ejector for not only soot measurement but also other use such as the dilution ratio or the mixing ratio is required to be adjusted.

SUMMARY OF THE INVENTION

The present claimed invention intends to solve the above-mentioned problems concerning dilution in measuring the exhaust gas, more concretely, desired objects are mainly (1) to make it possible to obtain a dilution ratio necessary for soot concentration measurement with a simple and low-cost arrangement by making use of the SOF measuring system with focusing attention on that both concentration of SOF and concentration of soot are measured in measuring diluted particulate matters, (2) to provide an exhaust gas analyzer that can easily change and adjust a dilution ratio in case of diluting the exhaust gas conducted at a time of soot measurement and to provide a superior mixing system that can be used broadly for diluting and mixing gas. It is not until the inventor of the present claimed invention found out that there was an area where flow of sample gas almost never changed even though flow of the dilution gas was changed as a result of keen examination that the problem (2) is solved.

First, regarding the problem (1), an exhaust gas analyzer in accordance with this present claimed invention comprises the following requirement.

I. An SOF measuring system that can continuously measure concentration of SOF in exhaust gas and a soot measuring system that can continuously measure concentration of soot in the exhaust gas are connected with an exhaust gas line through which a part or all of the exhaust gas discharged from an internal combustion engine flows.

II. The soot measuring system comprises
  a) a diluter that selectively dilutes either one of the exhaust gas and standard gas whose hydrocarbon concentration is known with diluent gas and extrudes it,
  b) a dilution ratio adjusting device that can adjust a dilution ratio of the diluter, and
  c) a soot detector that detects soot in the exhaust gas or the standard gas diluted by the diluter.

III. The SOF measuring system can measure hydrocarbon concentration in the standard gas diluted by the diluter with an arrangement that the SOF measuring system can be connected with the diluter, and the dilution ratio of the diluter at this state can be calculated based on the hydrocarbon concentration in the standard gas after dilution when the dilution ratio adjusting device is operated by a certain amount.

In accordance with this arrangement, it is possible to obtain the dilution ratio of the diluter at a time of soot measurement by the use of the standard gas at a time prior to or after soot measurement and to calculate the concentration of soot in the exhaust gas prior to dilution based on the obtained dilution ratio and the concentration of soot in the diluted exhaust gas detected by the soot detector with an arrangement of a simple flow path wherein the piping is bifurcated from the diluter to be connected with the existing SOF measuring system, the piping to connect the standard gas source is connected with the diluter, or the switch valves are arranged on the piping.

The diluter might be clogged with soot if a fluid path inside of the diluter has a complicated arrangement because soot flows in the diluter. In addition, if there is pulsation generating in the flow at a time of dilution, the pulsation might be a cause of an error of measurement by the soot detector. Then in order to make the diluter that is free from pulsation at a time of dilution with a simple arrangement, it is preferable that the diluter comprises a narrow part whose flow path diameter is narrowed and a diffusible part whose flow path diameter is extended and that is serially arranged to the narrow part, the diluent gas is accelerated to be negative-pressured by passing the diluent gas through the narrow part and the diffusible part, and the exhaust gas or the standard gas is sucked because the diluent gas is negative-pressured so that the exhaust gas or the standard gas is mixed with the diluent gas. It would be further more preferable from a viewpoint of mixing if a diffusible part is serially arranged downstream of the narrow part.

As a concrete embodiment of the dilution ratio adjusting device represented is a pressure regulator that adjusts pressure of the diluent gas introduced into the diluter.

As a soot detector that can high-sensitively and continuously measure soot represented is the soot detector comprising an electric charge imparting part that imparts electric charge to soot and an electric charge measuring part that measures a quantity of electric charge of soot.

As the SOF measuring system suitable for soot measurement in accordance with this invention represented is the SOF measuring system comprising a bifurcated part that bifurcates the introduced exhaust gas, a particle component removing line that sets one of the bifurcated exhaust gas at a measurement reference temperature for SOF measurement and removes particle component in the exhaust gas kept at the measurement reference temperature, a passing line that passes other bifurcated exhaust gas, and hydrocarbon concentration detectors each of which continuously detects hydrocarbon concentration in the exhaust gas sent out from the particle component removing line and the passing line respectively, and the SOF measuring system is so arranged that the SOF concentration in the exhaust gas can be calculated based on a difference between the hydrocarbon concentration detected by one of the hydrocarbon concentration detectors and the hydrocarbon concentration detected by the other hydrocarbon concentration detector. The term here "particle component" is mainly hydrocarbon particle liquefied or solidified in gas.

The hydrocarbon concentration detector is especially preferably a hydrogen flame ionization detector. In case that the SOF measuring system is arranged by the use of the hydrogen flame ionization detector, soot is detected in a spike-like peak state, if an output from the hydrogen flame ionization detector locating at a side of a passing line is graphed. As a result, it is possible, for example, to verify the concentration of soot measured by the soot measuring system.

In order to measure the concentration of soot in the exhaust gas by making use of the exhaust gas analyzer in accordance with this invention, it is preferable that the hydrocarbon concentration of the diluted standard gas is measured by the SOF measuring system, the dilution ratio of the diluter is calculated based on a ratio of the hydrocarbon concentration of the diluted standard gas to the hydrocarbon concentration of the standard gas prior to dilution, a correlation between the dilution ratio and an operated amount is obtained based on the operated amount of the dilution ratio adjusting device at that time, the dilution ratio is adjusted so as to become a desired value at a time of soot measurement by operating the dilution ratio adjusting device by the operated amount obtained from the correlation, or the dilution ratio is obtained based on the operated amount of the dilution ratio adjusting device set at a time of soot measurement and the correlation, and the concentration of soot in the exhaust gas is calculated based on the dilution ratio and the measured result by the soot detector.

In accordance with this invention, it is possible to obtain the dilution ratio of the exhaust gas necessary for measuring the concentration of soot accurately just with the simple flow path by making use of the SOF measuring system together with the soot measuring system in case of measuring the particulate matter.

Next, regarding the problem (2), the exhaust gas analyzer in accordance with the present claimed invention is so arranged that a soot measuring system that can measure soot is connected with an exhaust gas line through which a part or all of exhaust gas discharged from an internal combustion engine flows, and characterized by that the soot measuring system comprises a diluter that dilutes the exhaust gas with diluent gas and extrudes it, a dilution ratio adjusting device that can adjust the dilution ratio of the diluter, and a soot detector that detects soot in the exhaust gas diluted by the diluter, wherein the diluter is so arranged that a narrow part whose flow path diameter is narrowed and a diffusible part whose flow path diameter is extended are serially arranged on an internal main path through which the diluent gas passes so as to form a negative-pressure area that is negative-pressured because the diluent gas is accelerated, and the diluter sucks the exhaust gas through a communicating path communicating with the negative-pressure area, mixes the exhaust gas with the diluent gas and then extrudes it, and the dilution ratio adjusting device changes a flow amount of the diluent gas introduced into the diluter within a range where a flow amount of the exhaust gas sucked by the diluter is kept generally constant by a predetermined operation from outside.

In accordance with this arrangement, since the dilution ratio can be easily adjusted by the use of the dilution system so that concentration of varieties of exhaust gas becomes appropriate for the soot detection, it is possible to measure the concentration of soot by the use of the high-precision soot detector. In addition, a possibility that the fluid path is clogged with soot can be avoided as much as possible because of a merit of the diluter of this type, namely the simple fluid path. Furthermore, the diluted exhaust gas can be sent out to the soot detector in a stable state without fail because of a merit that the diluter has no pulsation that prevents the accurate concentration measurement.

As a soot detector whose effect can especially be significant when the present claimed invention is applied represented is the soot detector comprising an electric charge imparting part that imparts electric charge to soot and an electric charge measuring part that measures electric charge of soot.

In order to simultaneously detect SOF as well as soot contained in the exhaust gas, it is preferable that an SOF measuring system that can measure concentration of SOF is further connected with the exhaust gas line. As the SOF measuring system in this case, it is preferable that the SOF measuring system comprises a bifurcated part that bifurcates the introduced exhaust gas, a particle component removing line that sets one of the bifurcated exhaust gas at a measurement reference temperature and removes particle component in the exhaust gas kept at the measurement reference temperature, a passing line that passes other bifurcated exhaust gas, and hydrocarbon concentration detectors each of which continuously detects hydrocarbon concentration in the exhaust gas sent out from the particle component removing line and the passing line respectively, and the SOF is so arranged that the SOF concentration in the exhaust gas can be calculated based on a difference between the hydrocarbon concentration detected by one of the hydrocarbon concentration detectors and the hydrocarbon concentration detected by the other hydrocarbon concentration detector.

The term here "particle component" is mainly hydrocarbon particle liquefied or solidified in gas.

The hydrocarbon concentration detector is especially preferably a hydrogen flame ionization detector. In case that the SOF measuring system is arranged by the use of the hydrogen flame ionization detector, soot is detected in a spike-like peak state, if an output from the hydrogen flame ionization detector locating at a side of a passing line is graphed. As a result, it is possible, for example, to verify the concentration of soot measured by the soot measuring system and to set up a standard of an optimum dilution ratio based on its result.

Since an object to be measured by the soot detector is the diluted exhaust gas, it is necessary to grasp a dilution ratio finally in order to measure the concentration of soot in the exhaust gas.

Then in order to make it possible to obtain the dilution ratio accurately with a simple arrangement by making use of the SOF measuring system it is preferable that the diluter is arranged to selectively introduce either one of the exhaust gas and standard gas whose hydrocarbon concentration is known so that the selected gas can be diluted, the SOF measuring system can measure concentration of hydrocarbon in the standard gas diluted by the diluter with an arrangement that the SOF measuring system can be connected with the diluter, and the dilution ratio of the diluter at this state can be calculated based on the concentration of hydrocarbon in the standard gas after dilution when the dilution ratio adjusting device is operated by a certain amount.

In addition, the present claimed invention can be applied broadly as a gas mixing system including diluting gas without being limited to the soot measurement. More specifically, the mixing system in accordance with the present claimed invention comprises a mixer where a narrow part whose flow path diameter is narrowed and a diffusible part whose flow path diameter is extended are serially arranged on an internal main path through which mixing gas as being gas to mix passes so as to form a negative-pressure area that is negative-pressured because the mixing gas is accelerated, and the mixing system sucks mixed gas as being gas to be mixed through a communicating path communicating with the negative-pressure area, mixes the mixed gas with the mixing gas and then extrudes it, and a mixing ratio adjusting device that changes a flow amount of the mixing gas introduced into the mixer within a range where a flow amount of the mixed gas sucked by the mixer is kept generally constant by a predetermined operation from outside.

In accordance with the mixing system, it is possible to adjust the mixing ratio easily by the use of the mixing ratio adjusting device in addition to mix the mixed gas with the mixing gas in a stable state because the flow path of the mixer is simple and free from pulsation.

In order to make this effect further more remarkably, it is preferable to further comprise a gas component detector that is connected with a gas extruding port of the mixer and that can continuously detect a component of the mixed gas.

As a concrete embodiment of the mixing ratio adjusting device represented is the mixing ratio adjusting device comprising a pressure regulator arranged on a mixing gas line through which the mixing gas flows, and a flow rate of the mixing gas introduced into the mixer from the mixing gas line is changed by an operation to adjust the pressure of the pressure regulator.

In case of using this mixing system as the diluting system, the diluent gas corresponds to the mixing gas, the exhaust gas corresponds to the mixed gas, the diluter corresponds to the mixer, the dilution ratio adjusting device corresponds to the mixing ratio adjusting device, and the gas component detector corresponds to the soot detector.

As mentioned above, in accordance with this invention, it is possible to change and adjust the dilution (mixing) ratio easily and to stabilize quality of the diluted (mixed) gas without pulsation.

DETAILED DESCRIPTION OF THE PREFERRED EMBODIMENTS

An exhaust gas analyzer in accordance with one embodiment of the present claimed invention will be described in detail with reference to the accompanying drawings.

(1) Overall Configuration of the Exhaust Gas Analyzer

Figure 1:
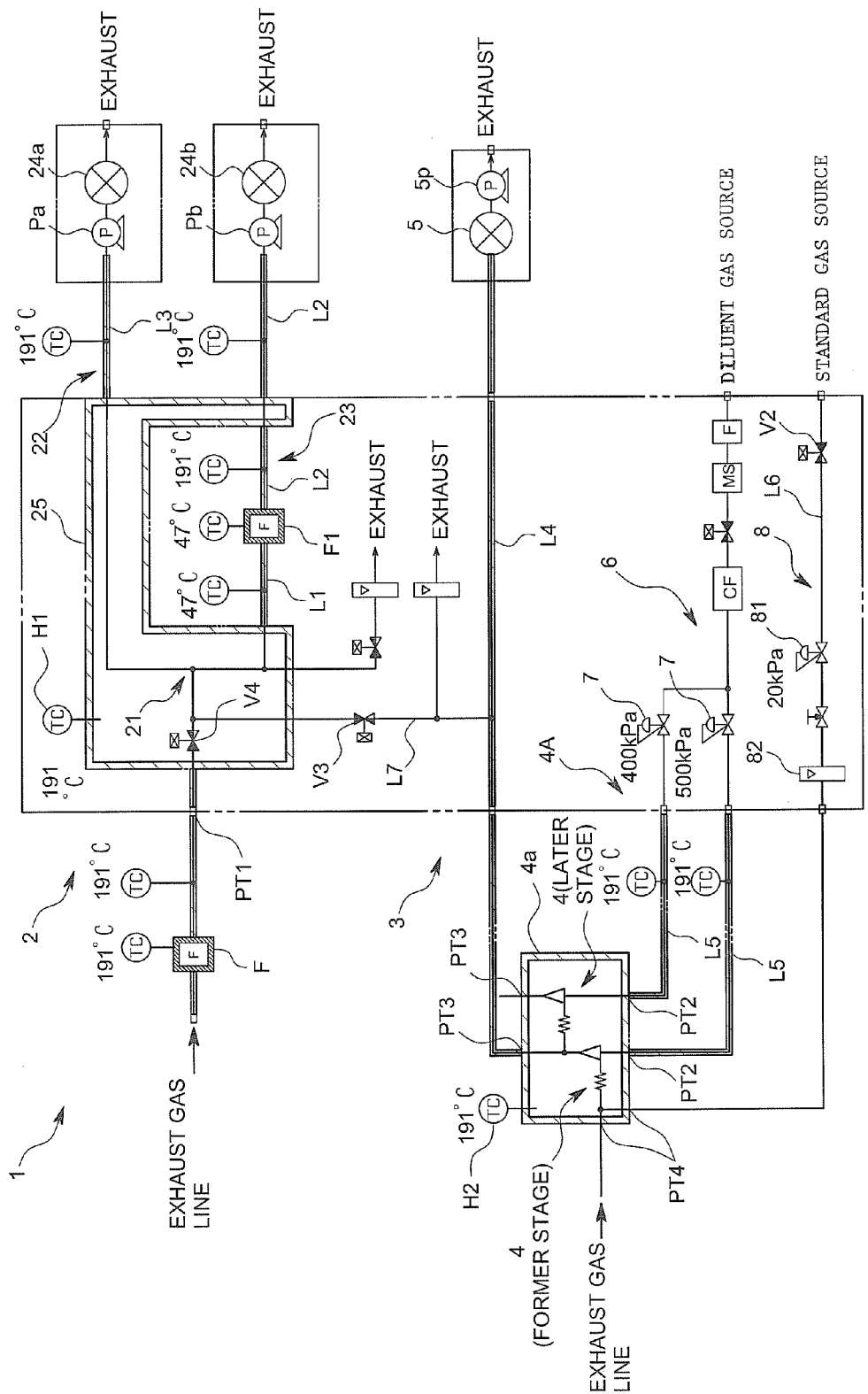
FIG. 1 is an overall fluid circuit diagram of an exhaust gas analyzer in accordance with one embodiment of the present claimed invention.

The exhaust gas analyzer 1 in accordance with this embodiment is to measure mass concentration of SOF (soluble organic fraction) and soot contained in exhaust gas of a diesel engine (not shown in drawings) as being an internal combustion engine and, as shown in FIG. 1, comprises an SOF measuring system 2 that can continuously measure mass concentration of SOF and a soot measuring system 3 that can continuously measure mass concentration of soot, each of which is connected in parallel with an exhaust gas line (not shown in drawings) to which a part or all of the exhaust gas is discharged from the diesel engine.

(2) SOF Measuring System

First, the SOF measuring 2 system will be explained.

The SOF measuring system 2 comprises, as shown in FIG. 1, a bifurcated part 21 that bifurcates the exhaust gas introduced from the exhaust gas line, a passing line 22 and a particle composition removal line 23 into each of which the exhaust gas bifurcated by the bifurcated part 21 is introduced respectively, and hydrogen flame ionization detectors 24a, 24b each of which is connected with each of the passing line 22 and the particle composition removal line 23 respectively through pumps Pa, Pb.

The bifurcated part 21 is formed by making use of a manifold block 25 having a fluid path bifurcating internally, and the exhaust gas line is connected with a gas introducing port PT1 as being an introducing port of the manifold block 25 through a temperature control pipe L such as a hot hose pipe heated to a predetermined temperature (approximate 191° C.) or a particulate matter removal filter F. A temperature controller H1 such as a heater that can control temperature is mounted on the manifold block 25 and the manifold 25 is kept at, for example, the predetermined temperature (approximate 191° C.).

The particle composition removal line 23 sets a temperature of the exhaust gas flowing internally at 47° C.±5° C. as a measurement standard temperature ordained by the 2007 EPA regulation, removes hydrocarbon (SOF) that liquidized or solidified at this temperature and extrudes the exhaust gas after the hydrocarbon is removed to the hydrogen flame ionization detector 24b.

More concretely, the particle composition removal line 23 is connected with the gas introducing port PT1 through the manifold block 25, and comprises a first temperature control pipe L1 heated to the measurement standard temperature, a filter F1 connected with a terminal of the first temperature control pipe L1, and a second temperature control pipe L2 that introduces the gas passing the filter F1 into the hydrogen flame ionization detector 24b. The second temperature control pipe L2 is heated to, for example, the predetermined temperature (approximate 191° C.).

The passing line 22 extrudes the exhaust gas heated to the predetermined temperature higher than the measurement standard temperature, more concretely 191° C. directly to the hydrogen flame ionization detector 24a, and comprises a third temperature control pipe L3 connected with the gas introducing port PT1 through the manifold block 25. The third temperature control pipe L3 is heated to the predetermined temperature (approximate 191° C.) and connected with the hydrogen flame ionization detector 24a.

The hydrogen flame ionization detector 24a, 24b is to continuously and real-time detect mass concentration of hydrocarbon contained in sample gas (the exhaust gas in the above case) by flowing the sample gas. The hydrogen flame ionization detector 24a, 24b ionizes the hydrocarbon in the sample gas by passing the sample gas (the exhaust gas in this case) through the hydrogen flame and detects and outputs its ionic current. An output value of the detecting signal shows the mass concentration of hydrocarbon.

In accordance with this arrangement, since a base line value of the detecting signal by the hydrogen flame ionization detector 24a connected with the passing line 22 shows the mass concentration of hydrocarbon in a vaporized condition at the predetermined temperature (191° C.) and a base line value of the detecting signal by the hydrogen flame ionization detector 24b connected with the particle composition removal line 23 shows mass concentration of vaporized hydrocarbon at the measurement standard temperature (47° C.±5° C.) is possible to measure the mass concentration of hydrocarbon condensed from the gaseous body to the liquid body or to the solid body between (47° C.±5° C.) and 191° C., namely the mass concentration of SOF in the exhaust gas by obtaining a difference between the values of the detecting signal by each of the hydrogen flame ionization detectors 24a, 24b.

In this embodiment, an information processing unit, not shown in drawings, receives the hydrocarbon detecting signals from the hydrogen flame ionization detectors 24a, 24b respectively, and calculates the mass concentration of SOF by obtaining a difference between the values shown by the hydrocarbon detecting signals and outputs the mass concentration of SOF to a display or the like.

(3) Soot Measuring System

Next, the soot measuring system 3 will be explained.

The soot measuring system 3 comprises, as shown in FIG. 1, a diluting system 4A that dilutes the exhaust gas with air as being diluent gas and sends it out and a soot detector 5 that detects mass concentration of soot in the diluted gas.

Figure 2:
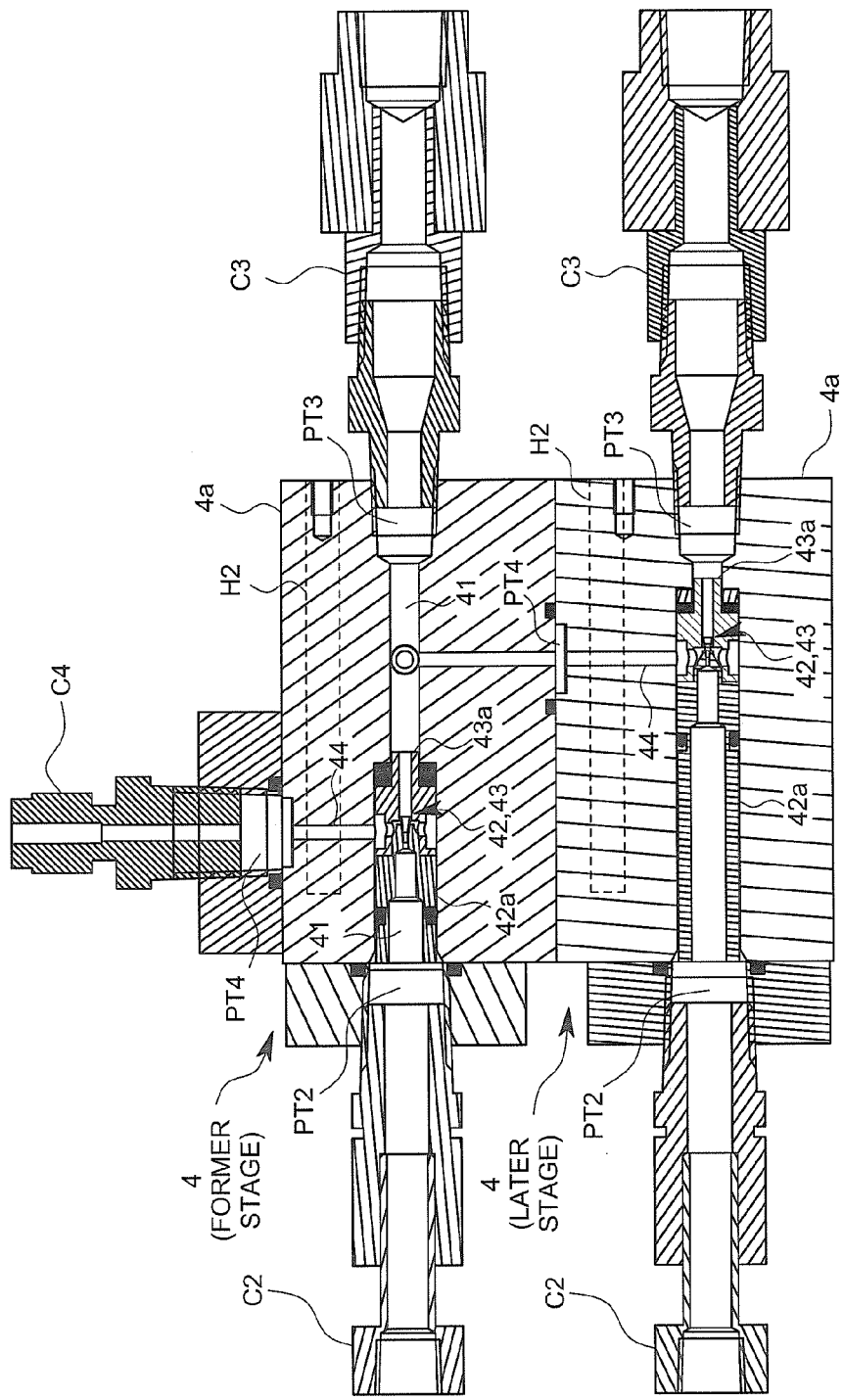
FIG. 2 is a cross-sectional view showing an internal structure of a diluter in accordance with this embodiment.
Figure 3:
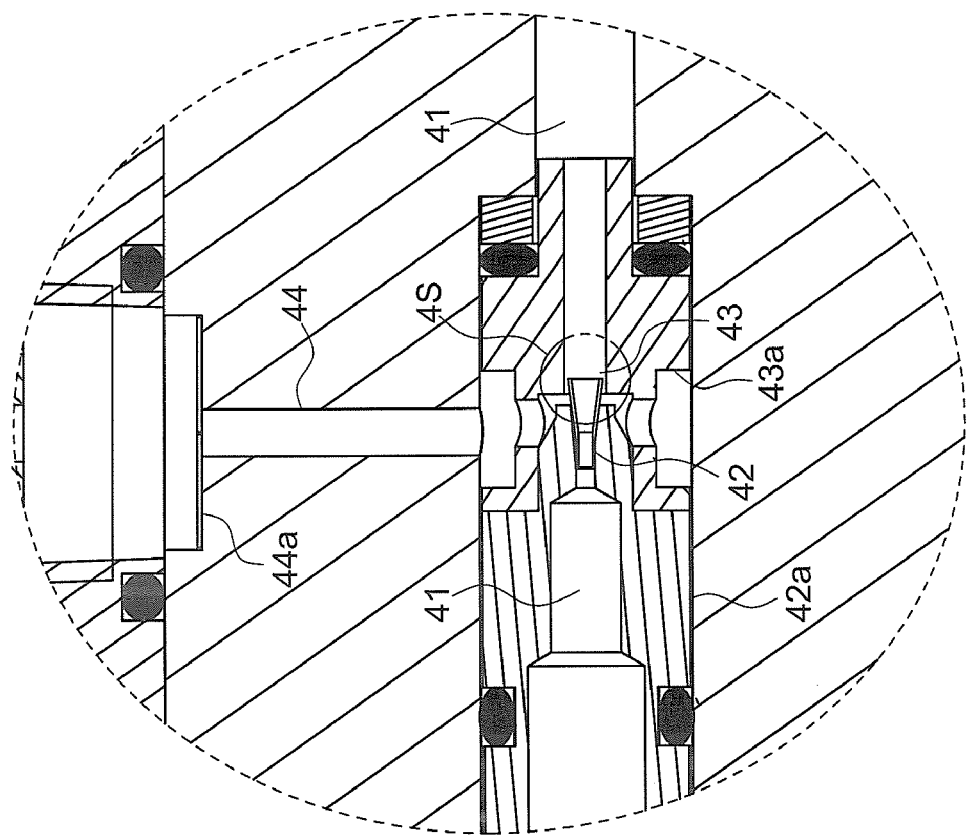
FIG. 3 is a cross-sectional view of an enlarged portion mainly showing a nozzle, a diffuser and an orifice of the diluter in accordance with this embodiment.

The diluting system 4A comprises, as shown in FIG. 1 through FIG. 3, a diluter 4 and a pressure regulator 7 as being a dilution ratio adjusting device.

The diluter 4 is an ejector-type, whose detail is shown in FIG. 2 and FIG. 3, wherein a nozzle 42 as being a narrow part whose flow path diameter is narrowed along a direction of a gas flow and a diffuser 43 as being a diffusible part whose flow path diameter is extended are arranged in this order serially on an internal main path 41 through which the diluent gas flows so as to form a negative-pressure area 4S that is negative-pressurized because the diluent gas is accelerated, and the sample gas is sucked through a communicating path 44 communicating to the negative-pressure area 4S, mixed with the diluent gas and then sent out. The nozzle is used as the narrow part and the diffuser is used as the diffusible part in this embodiment, however, various substitutes such as an orifice or a venturi tube may be used.

More specifically, the diluter 4 mainly comprises a piping block body 4a having the communicating path 44 communicating to the main path 41 and the negative-pressure area 4S, a nozzle member 42a that forms the nozzle 42 by being inserted into the main path 41, a diffuser member 43a that forms the diffuser 43 by being inserted into the main path 41, an inlet port PT2 as being an inlet of the main path 41, an outlet port PT3 as being an outlet of the main path 41, a sample gas introducing port PT4 as being an inlet of the communicating path 44, and joints for coupling C2, C3, C4 arranged on the inlet port PT2, the outlet port PT3 and the sample gas introducing port PT4 respectively.

A temperature controller H2 such as a heater that can adjust temperature is mounted on the piping block body 4a and the diluter 4 is heated to the predetermined temperature (approximate 191° C.). This is to volatize SOF or the like (especially SOF that attaches to soot) contained in the exhaust gas so as to prevent an adverse effect on soot measurement by a soot detector 5, to be described later. Since the soot detector 5 is a type incapable of introducing high-temperature gas, the temperature of the diluted exhaust gas is lowered during passing through a piping L4 from the outlet port PT3 of the diluter 4 to the soot detector 5. SOF that has once vaporized will never be separated out again as a particle that has influence on the measurement because SOF is diluted even though the temperature of the diluted exhaust gas is lowered.

In addition, a portion to be directly connected with the inlet port PT2 of a diluent gas line 6 is heated to the predetermined temperature (approximate 191° C.) by the use of a fourth temperature control pipe L5 so as to stabilize air flow to be supplied.

Furthermore, as shown in FIG. 1, the diluent gas line 6 through which the diluent gas passes is connected with the inlet port PT2 so as to introduce air as being the diluent gas, and the exhaust gas line is connected with the sample gas introducing port PT4. In addition, the soot detector 5 is connected with the outlet port PT3 through the piping L4 so that the diluted gas can be sent out to the soot detector 5.

In addition, an orifice ring 44a as being a flow limit member is exchangeably mounted, as shown in FIG. 3, at least on the communicating path 44 of the diluter 4 locating in a former stage.

A diluent gas source (not shown in drawings) such as a compressor or a steel bottle is connected with a leading end of the diluent gas line 6 and the pressure regulator 7 as being a dilution ratio adjusting device is arranged on the diluent gas line 6 so that the dilution ratio can be adjusted by controlling pressure of the air flowing into the inlet port PT2.

The pressure regulator 7 is arranged on the diluent gas line 6 and controls the pressure of the air flowing into the inlet port PT2 of the diluter 4 so as to control its air flow.

However, generally it is not possible for a diluter of ejector-type to change a dilution ratio arbitrarily. This is based on a fact that the pressure in the negative-area 4S decreases if a lot of diluent gas (for example, air) is flowed and therefore the flow volume of the sample gas increases by just this much. As a result of this, the dilution ratio does not fluctuate significantly.

Figure 4:
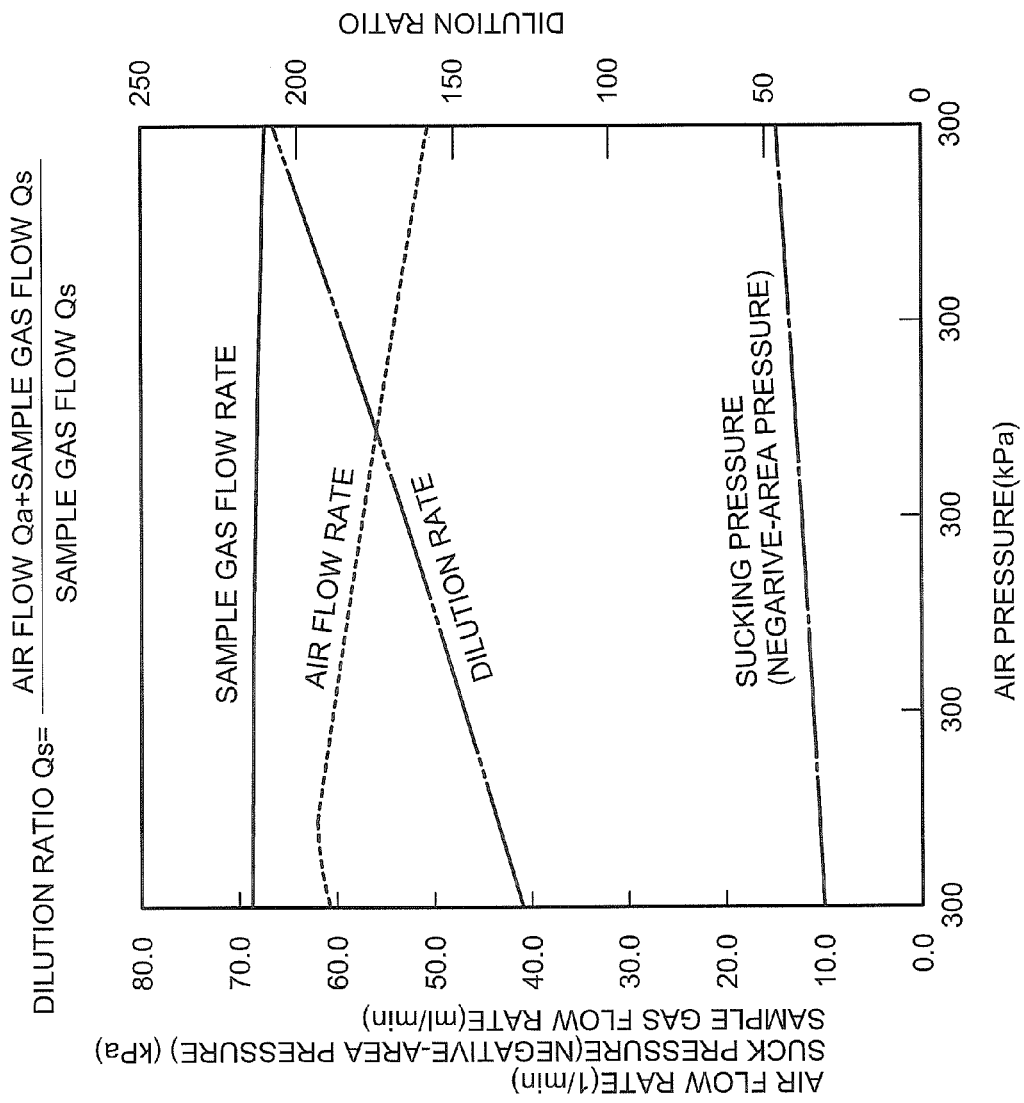
FIG. 4 is a graph showing a characteristic of the diluter in accordance with this embodiment.

Then in this embodiment, as shown in FIG. 4, an operation range of the pressure regulator 7, namely a pressure adjustable range is restricted to a range where the sucked flow of the sample gas in the diluter 4 is kept generally constant due to pressure adjustment even if the flow of the diluent gas introduced into the diluter 4 changes. More concretely, a range of the air pressure is between 300 kPa through 500 kPa. It is a matter of course that this range depends on a shape or a size of the nozzle or the diffuser, or a diameter of the orifice, however, it is not until this range is used that the pressure regulator 7 acts as the dilution ratio adjusting device and the dilution ratio can be changed by the operation of the pressure setting.

In this embodiment, in order to broaden a range to adjust the dilution ratio, the diluters 4 are connected serially in plural (two) stages. More specifically, the outlet port PT3 of the diluter 4 locating in a former stage is connected with the sample gas introducing port PT4 of the diluter 4 locating in a later stage so that dilution can be conducted in plural stages. As a result, the dilution ratio can be changed in compliance with an order by selecting which outlet port PT3 is to be used.

In accordance with the diluting system 4A of this embodiment, it is possible to adjust the dilution ratio easily so that the high-precision soot detector can maintain appropriate mass concentration of soot to exert its performance fully with maintaining merits of the diluter 4, namely merits wherein the flow path is prevented from being clogged with soot and free from pulsation.

Figure 5:
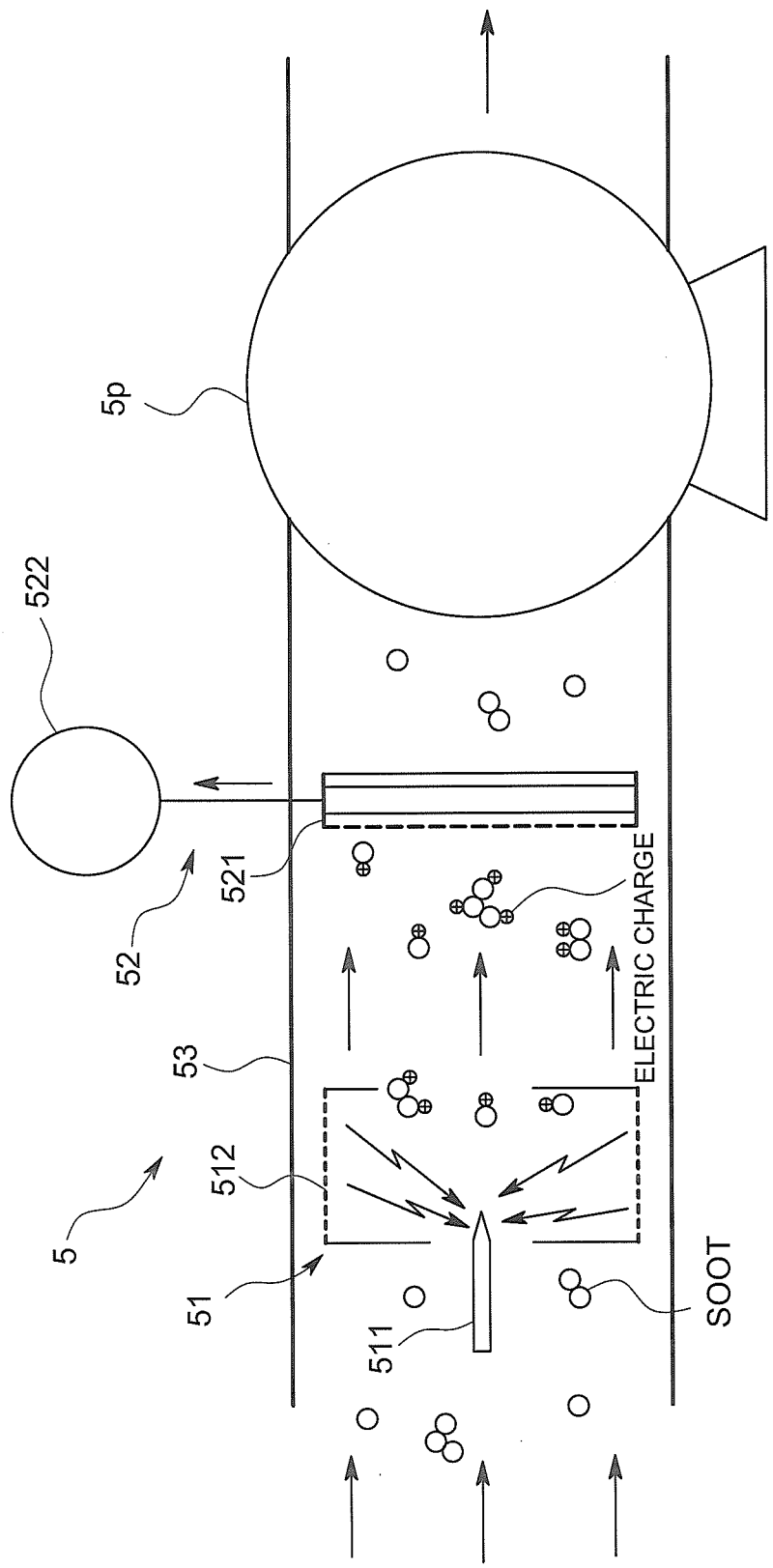
FIG. 5 is a pattern diagram of a soot detector in accordance with this embodiment.

The soot detector 5 comprises, whose pattern diagram is shown in FIG. 5, an electric charge imparting part 51 that imparts electric charge to soot contained in the sample gas and an electric charge measuring part 52 that measures electric charge of soot, and continuously and real-time measures soot contained in the diluted exhaust gas introduced as the sample gas.

The electric charge imparting part 51 is arranged on the flow path 53 of the introduced diluted exhaust gas, and comprises a positive electrode 511 and a negative electrode 512, wherein a potential difference between the positive electrode 511 and the negative electrode 512 is, for example, several thousands volt (5000 through 7000 volt). Corona discharge is generated between the positive electrode 511 and the negative electrode 512 due to its potential difference and the soot particle in the diluted exhaust gas is charged in proportion to its surface area as a result that the diluted exhaust gas passes between the positive electrode 511 and the negative electrode 512. As an example is shown in FIG. 5, the positive electrode 511 is in a thin shape of a pin type locating at a center of the flow path 53, and the negative electrode 512 is a cylindrical cancellous member arranged to surround the positive electrode 511. The electric charge imparting part 51 may have other arrangement, for example, the electric charge is imparted by irradiating ultraviolet rays.

The electric charge measuring part 52 comprises a capturing member 521 such as a metal plate arranged downstream of the electric charge imparting part 51 in the flow path 53 and a current detector 522 that measures a value of the current that soot captured by the capturing member 521 flows and outputs soot detecting signal showing its value. The value of the soot detecting signal expresses a surface area of the soot particles because the quantity of electric charge is proportional to a surface area of the soot particles. In addition, since there is a predetermined relational expression between the surface area of the soot particles and the mass of the soot particles, the mass of the soot particles, consequently concentration of soot in the diluted exhaust gas can be calculated from the value of the detecting signal.

However, what required finally is concentration of soot in the exhaust gas prior to dilution, and it is necessary to grasp the dilution ratio by the diluter 4 in addition to measured data of the concentration of soot in the diluted exhaust gas in order to measure the concentration of soot in the exhaust gas prior to dilution.

Then in this embodiment, as shown in FIG. 1, it is so arranged that a standard gas line 8 through which standard gas (for example, air containing $C_3H_8$) whose hydrocarbon concentration is known flows and the exhaust gas line can be switched to be connected with the sample gas introducing port PT4 of the diluter 4, and the outlet port PT3 of the diluter 4 and the exhaust gas line can be switched to be connected with the gas introducing port PT1 of the SOF measuring system 2.

More specifically, connection of the standard gas line 8 and the exhaust gas line with the sample gas introducing port PT4 can be switched by providing a switch valve V2 on the piping L6 of the standard gas line 8 to the sample gas introducing port PT4 of the diluter 4. A standard gas source (such as a steel bottle) is connected with an inlet of the standard gas line 8, a pressure regulator 81 is arranged so that line pressure of downstream the pressure regulator 81 can be kept at a constant value and a flow instrument 82 is arranged so that flow of the standard gas introduced into the sample gas introducing port PT4 can be monitored.

A switch valve V3 is arranged on a connection piping L7 from the outlet port PT3 of the diluter 4 with the gas introducing port PT1 of the SOF measuring system 2, a switch valve V4 is arranged on a connection pipe of the exhaust gas line with the gas introducing port PT1, and either one of the outlet port PT3 of the diluter 4 and the exhaust gas line can be switched to be connected with the gas introducing port PT1 by alternative selection of the switch valves V3, V4.

In accordance with this arrangement, it is possible for either one of the hydrogen flame ionization detector 24a and the hydrogen flame ionization detector 24b to measure the hydrocarbon concentration of the diluted standard gas by making the standard gas diluted by the diluter 4 flow into the SOF measuring system 2 with an operation of the switch valves V3, V4. Then the dilution ratio of the diluter 4 at that time can be obtained based on the measured hydrocarbon concentration of the diluted standard gas and the known hydrocarbon concentration of the standard gas, and then the concentration of soot in the exhaust gas can be calculated based on the dilution ratio and the concentration of soot in the diluted exhaust gas.

Furthermore, in this embodiment, an information processing unit, not shown in drawings, receives the soot detecting signal and the hydrocarbon detecting signal output by the hydrogen flame ionization detector 24a (24b) at a time when the diluted standard gas is flowed, and outputs the concentration of soot automatically calculated based on these values and the previously memorized known concentration data of the standard gas to a display or the like. In addition, each of the switch valves V2, V3, V4 is of an electromagnetic drive type and driven to open or close by a valve driving signal output by the information processing unit.

(4) Usage of the Exhaust Gas Analyzer

Next, one example of a method for measuring the concentration of soot by making use of the exhaust gas analyzer 1 will be concretely explained. A case that the information processing unit automatically measures the concentration of soot in accordance with a program will be explained with reference to FIG. 6 and FIG. 7.

(Drawing Up an Analytical Curve)

Figure 6:
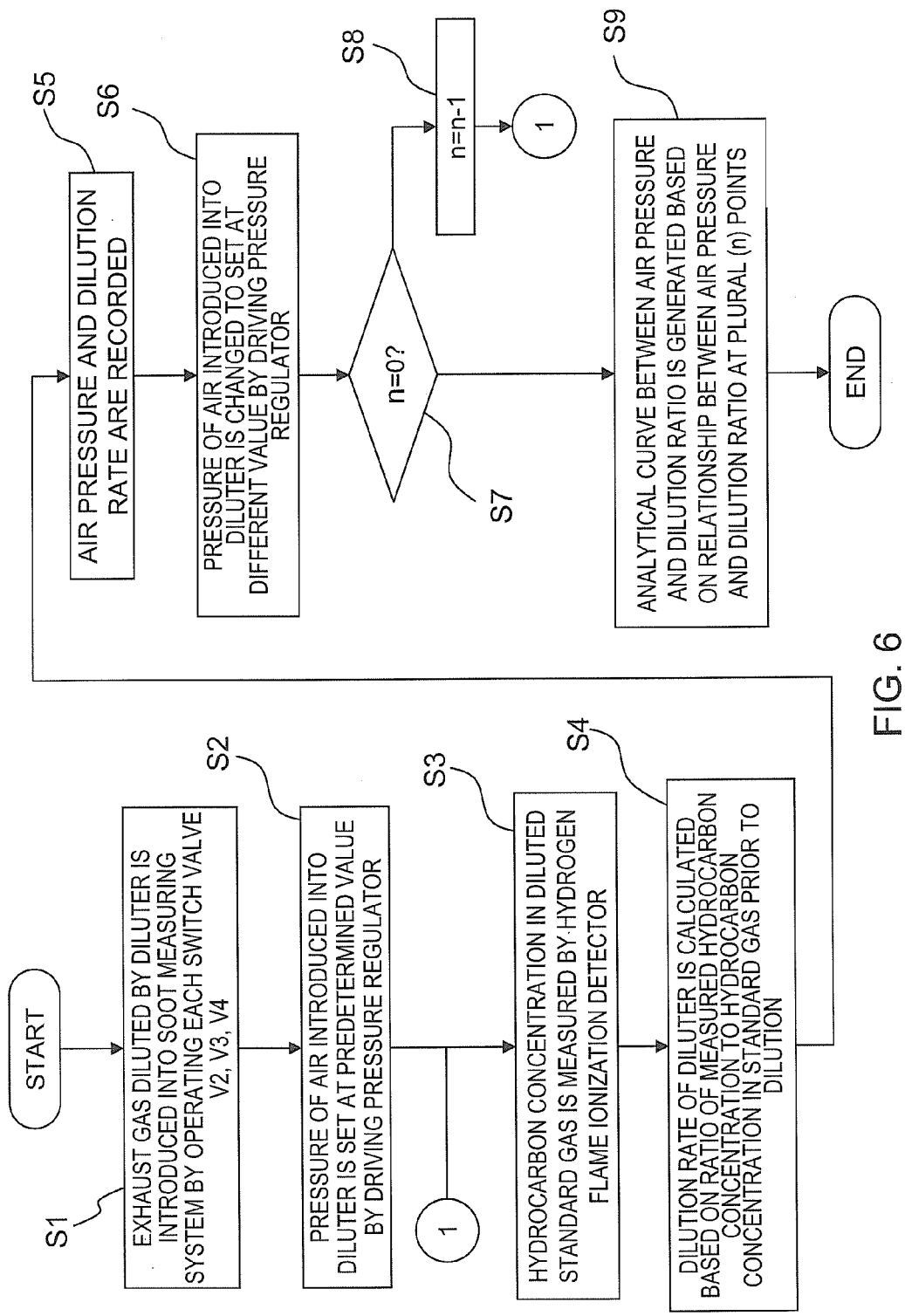
FIG. 6 is a flow chart showing a method for measuring soot by making use of the exhaust gas analyzer in accordance with this embodiment.

First, the standard gas is introduced into the SOF measuring system 2 through the diluter 4 by operating each of the switch valves V2, V3, V4 to open or close with the valve driving signal output to each of the switch valves V2, V3, V4 (FIG. 6: Step S1).

The air introduced into the diluter 4 is kept at a predetermined pressure by giving a driving signal to the pressure regulator 7 (Step S2).

With this state kept, the hydrocarbon concentration in the diluted standard gas is measured by the hydrogen flame ionization detector 24a (24b) (Step S3).

The dilution ratio of the diluter 4 is calculated based on a ratio of the hydrocarbon concentration in the diluted standard gas to the hydrocarbon concentration in the standard gas prior to dilution (Step S4), and the dilution ratio and the air pressure are recorded in pairs (Step S5).

Next, a pressure of air introduced into the diluter 4 is changed to set at a different value by changing a value of the driving signal to the pressure regulator 7 (Step S6) and the step S3 through the step S6 are repeated at plural times (n times) (Step S7, S8).

An analytical curve between the pressure and the dilution ratio (relative relationship) is drawn up based on a relationship between values of the pressure measured at plural points and the dilution ratio and then stored in a predetermined area of the memory (Step S9).

(Soot Concentration Measurement)

Figure 7:
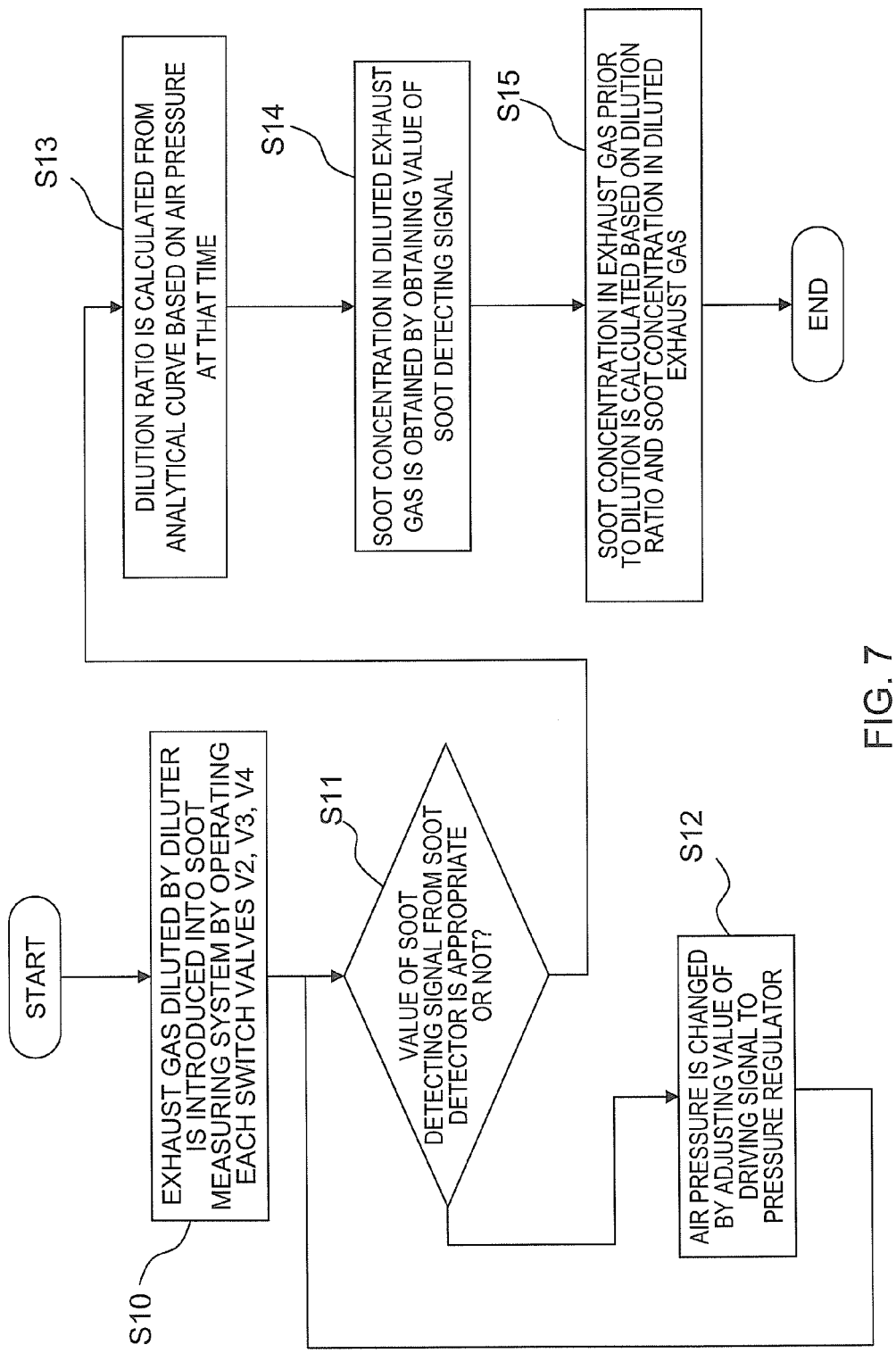
FIG. 7 is a flow chart showing a method for measuring soot by making use of the exhaust gas analyzer in accordance with this embodiment.

First, the exhaust gas is introduced into the soot measuring system 3 by operating each of the switch valves V2, V3, V4 to open or close (FIG. 7: Step S10)

Because the concentration of soot in the exhaust gas is unknown, the value of the driving signal to the pressure regulator 7 is changed with reference to a value of the soot detecting signal from the soot detector 5 so that the pressure of the diluent gas line 6 is set to be suitable for the soot concentration measurement (Step S11, S12).

The dilution ratio at that time is calculated based on the set value of the air pressure and the analytical curve (Step S13).

The soot concentration in the diluted exhaust gas is obtained by applying a predetermined relational expression stored in the memory to the value of the soot detecting signal (Step S14).

Finally, the concentration of soot in the exhaust gas is calculated based on the concentration of soot in the diluted exhaust gas and the dilution ratio (Step S15).

The method for measuring the concentration of soot is mentioned above, and may be others, for example, the analytical curve is not drawn up, the dilution ratio at the set value of the pressure of the diluent gas at that time is calculated by the use of the standard gas every time the concentration of soot is measured and the concentration of soot is calculated based on the dilution ratio.

In addition, all of the above-mentioned actions may be operated manually by an operator, or a part of them may be automatically operated and other may be operated manually.

As a result, in accordance with the exhaust gas analyzer 1, it is possible to obtain the dilution ratio of the diluter 4 at a time of soot measurement by the use of the standard gas at a time prior to or after soot measurement and to calculate the concentration of soot in the exhaust gas prior to dilution based on the obtained dilution ratio and the concentration of soot in the diluted exhaust gas detected by the soot detector with a simple arrangement of a flow path wherein the piping is bifurcated from the diluter 4 to be connected with the existing SOF measuring system 2, the piping to connect the standard gas source is connected with the diluter 4, or the switch valves V2, V3, V4 are arranged on the piping.

In addition, since the dilution ratio can be easily adjusted by the use of the dilution system 4A so that concentration of varieties of exhaust gas becomes appropriate for the soot detection, it is possible to measure the concentration of soot by the use of the high-precision soot detector 5. In addition, a possibility that the fluid path is clogged with soot can be avoided as much as possible because of a merit of the diluter 4 of this type, namely the simple fluid path. Furthermore, the diluted exhaust gas can be sent out to the soot detector in a stable state without fail because of a merit that the diluter 4 has no pulsation that prevents the accurate concentration measurement.

Furthermore, since the hydrogen flame ionization detector 24a, 24b detects soot in a spike-like peak state, it is possible, for example, to verify the concentration of soot measured by the soot measuring system and to set up a standard of an optimum dilution ratio based on its result.

The present claimed invention is not limited to the above-mentioned embodiment. For example, the hydrocarbon detector or the soot detector may utilize other principle, or the exhaust gas line may introduce exhaust gas diluted by a full tunnel.

The diluter may have an arrangement of one stage, or of three or more stages. The diluter is not limited to be of the ejector type, and may be of other type such as a rotary pump type.

Furthermore, the dilution ratio adjusting device may utilize not only the pressure regulator but also a flow adjusting valve such as a valve.

In addition, this diluting system may be used for diluting or mixing other gas. Other arrangement may be variously modified without departing from a spirit of the present claimed invention such as the switch valve may be a three-way valve.

As mentioned above, the present claimed invention makes it possible to continuously and high-precisely measure the concentration of soot in exhaust gas with a simple and compact arrangement, which facilitates research and development of an internal combustion engine such as an automobile. In addition, it is possible to change and adjust the dilution (mixing) ratio easily as well as to stabilize quality of the diluted (mixed) gas free from pulsation. As a result, the present claimed invention can be broadly applied to a usage such as gas continuous measurement.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus comprising:

an exhaust gas analyzer connecting an SOF measuring system that can measure SOF in exhaust gas and a soot measuring system that can measure soot in the exhaust gas with an exhaust gas line through which a part or all of the exhaust gas discharged from an internal combustion engine flows;

wherein the soot measuring system includes a diluter having a sample introducing port connected with (i) a standard gas line through which standard gas whose hydrocarbon concentration is known and which is supplied from a standard gas source flows and (ii) the exhaust gas line, and which can be switched so as to selectively dilute either one of the exhaust gas and the standard gas with diluent gas and extrudes it, a dilution ratio adjusting device that can adjust a dilution ratio of the diluter, and a soot detector that detects soot in the exhaust gas or the standard gas diluted by the diluter;

the SOF measuring system can measure hydrocarbon concentration in the standard gas diluted by the diluter with an arrangement that the SOF measuring system can be connected with the diluter; and the dilution ratio of the diluter at this state can be calculated based on the hydrocarbon concentration in the standard gas after dilution when the dilution ratio adjusting device is operated by a certain amount.

2. The apparatus of claim 1, wherein the diluter comprises a narrow part whose flow path diameter is narrowed and a diffusible part whose flow path diameter is extended and that is serially arranged to the narrow part, the diluent gas being accelerated to be negative-pressured by passing the diluent gas through the narrow part and the diffusible part, and the exhaust gas or the standard gas being sucked because the diluent gas is negative-pressured so that the exhaust gas or the standard gas is mixed with the diluent gas.

3. The apparatus of claim 2, wherein the dilution ratio adjusting device is a pressure regulator that adjusts pressure of the diluent gas introduced into the diluter.

4. The apparatus of claim 1, wherein the soot detector comprises an electric charge imparting part that imparts electric charge to soot and an electric charge measuring part that measures a quantity of electric charge of soot.

5. The apparatus of claim 1, wherein the SOF measuring system comprises:

a bifurcated part that bifurcates the introduced exhaust gas;

a particle component removing line that sets one of the bifurcated exhaust gas at a measurement reference temperature for SOF measurement and removes particle component in the exhaust gas kept at the measurement reference temperature;

a passing line that passes other bifurcated exhaust gas;

hydrocarbon concentration detectors each of which continuously detects hydrocarbon concentration in the exhaust gas sent out from the particle component removing line and the passing line respectively; and the SOF measuring system is so arranged that the SOF concentration in the exhaust gas can be calculated based on a difference between the hydrocarbon concentration detected by one of the hydrocarbon concentration detectors and the hydrocarbon concentration detected by the other hydrocarbon concentration detector.

6. A method for measuring soot that makes use of the apparatus of claim 1, the method comprising:

supplying the standard gas from the standard gas source via the standard gas line;

diluting the standard gas;

measuring the hydrocarbon concentration of the diluted standard gas with the SOF measuring system;

calculating the dilution ratio of the diluter based on a ratio of the hydrocarbon concentration of the diluted standard gas to the hydrocarbon concentration of the standard gas prior to dilution;

obtaining a correlation between the dilution ratio and an operated amount based on the operated amount of the dilution ratio adjusting device at that time;

adjusting the dilution ratio to become a desired value at a time of soot measurement by operating the dilution ratio adjusting device by the operated amount obtained from the correlation, or the dilution ratio is obtained based on the operated amount of the dilution ratio adjusting device set at a time of soot measurement and the correlation; and calculating the concentration of soot in the exhaust gas based on the dilution ratio and the measured result by the soot detector.

7. The method of claim 6 wherein the standard gas is diluted by opening at least one valve operatively associated with the standard gas line and closing at least one valve operatively associated with the exhaust gas line.

8. The method of claim 7 further comprising diluting the exhaust gas by opening the at least one valve operatively associated with the exhaust gas line and closing the at least one valve operatively associated with the standard gas line.

9. An apparatus with an exhaust gas analyzer wherein a soot measuring system that can measure soot in exhaust gas is connected with an exhaust gas line through which a part or all of the exhaust gas discharged from an internal combustion engine flows, the improvement comprising:

the soot measuring system including a diluter having a sample introducing port connected with (i) a standard gas line through which standard gas whose hydrocarbon concentration is known and which is supplied from a standard gas source flows and (ii) the exhaust gas line, and which can be switched so as to selectively dilute either one of the exhaust gas and the standard gas with diluent gas which is compressed to be introduced to an internal main path and extrudes it, a dilution ratio adjusting device that can adjust the dilution ratio of the diluter, and a soot detector that detects soot in the exhaust gas or the standard gas diluted by the diluter;

the diluter being so arranged that a narrow part whose flow path diameter is narrowed and a diffusible part whose flow path diameter is extended are serially arranged on the internal main path through which the diluent gas passes so as to form a negative-pressure area that is negative-pressured because the diluent gas is accelerated, and the diluter sucks the exhaust gas through a communicating path communicating with the negative-pressure area, mixes the exhaust gas with the diluent gas and then extrudes it; and the dilution ratio adjusting device changes a flow amount of the diluent gas introduced into the diluter within a range where a flow amount of the exhaust gas sucked by the diluter is kept generally constant by a predetermined operation from outside.

10. The apparatus of claim 9, wherein the soot detector comprises an electric charge imparting part that imparts electric charge to soot and an electric charge measuring part that measures electric charge of soot.

11. The apparatus of claim 9, wherein an SOF measuring system that can measure SOF concentration is further connected with the exhaust gas line.

12. The apparatus of claim 11, wherein the SOF measuring system comprises:
- a bifurcated part that bifurcates the introduced exhaust gas;
- a particle component removing line that sets one of the bifurcated exhaust gas at a measurement reference temperature and removes particle component in the exhaust gas kept at the measurement reference temperature;
- a passing line that passes other bifurcated exhaust gas;
- hydrogen flame ionization detectors each of which continuously detects hydrocarbon concentration in the exhaust gas sent out from the particle component removing line and the passing line respectively; and
- the SOF is so arranged that the SOF concentration in the exhaust gas can be calculated based on a difference between the hydrocarbon concentration detected by one of the hydrogen flame ionization detectors and the hydrocarbon concentration detected by the other hydrogen flame ionization detector.

13. The apparatus of claim 11, wherein the diluter is arranged to selectively introduce either one of the exhaust gas and standard gas whose hydrocarbon concentration is known so that the selected gas can be diluted, the SOF measuring system can measure concentration of hydrocarbon in the standard gas diluted by the diluter with an arrangement that the SOF measuring system can be connected with the diluter, and the dilution ratio of the diluter at this state can be calculated based on the concentration of hydrocarbon in the standard gas after dilution when the dilution ratio adjusting device is operated by a certain amount.

* * * * *